United States Patent [19]

Fried

[11] Patent Number: 4,721,819

[45] Date of Patent: Jan. 26, 1988

[54] PROCESS FOR THE PREPARATION OF HIGHER ALLYLIC ETHERS

[75] Inventor: Herbert E. Fried, Houston, Tex.

[73] Assignee: Shell Oil Company, Houston, Tex.

[21] Appl. No.: 947,771

[22] Filed: Dec. 30, 1986

[51] Int. Cl.$^4$ ............................................. C07C 41/05
[52] U.S. Cl. .................................................... 568/675
[58] Field of Search ............................... 568/675, 689

[56] References Cited

U.S. PATENT DOCUMENTS 3,577,466  5/1971  Nozaki .

FOREIGN PATENT DOCUMENTS 913919  12/1962  United Kingdom .

Primary Examiner—Howard T. Mars

[57] ABSTRACT

In a process for the preparation of allylic ethers which comprises contacting and reacting an allylic alcohol reactant comprising one or more $C_6$ to $C_{20}$ allylic alcohols with a glycol reactant comprises one or more $C_2$ or $C_3$ alkylene glycols and their polyalkylene glycols in the presence of a cuprous salt catalyst and an acidic co-catalyst, the invention is the improvement which comprises contacting the allylic alcohol and alkylene glycol reactants in an agitated reaction mixture containing a solvent for the allylic alcohol reactant and the ether product which is substantially immiscible with the alkylene glycol reactant, said solvent being present in the reaction mixture in a quantity by weight which is at least about three times the weight of the allylic alcohol reactant. The improvement of the invention substantially increases the selectivity of the process for the production of the allylic ethers.

11 Claims, No Drawings

PROCESS FOR THE PREPARATION OF HIGHER ALLYLIC ETHERS

BACKGROUND OF THE INVENTION

This invention relates to a process for the conversion of higher allylic alcohols to allylic ethers by a coupling reaction with alkylene glycols.

The allylic ethers of interest to this invention are those produced by the coupling of higher allylic alcohols with alkylene glycols. This coupling reaction can be illustrated, for instance, by reactions of higher 2-alken-1-ols or 1-alkene-3-ols with ethylene glycol:

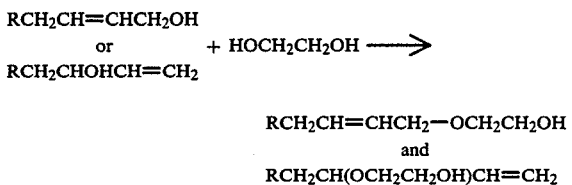

wherein R is an alkyl group of from about 3 to 17 carbon atoms. The higher carbon number allylic ethers of alkylene glycols have utility as chemical intermediates. The ethers are known to be useful in the preparation of valuable polymers by polymerization either alone or with vinyl monomers (e.g., ethylene, styrene, or acrylonitrile), and can also be used in the synthesis of nonionic and anionic surfactant products.

It is generally known in the art that such allylic ethers can be prepared by reaction of allylic alcohols with one or more alkylene glycols (including polyalkylene glycols) selected from the group consisting of ethylene glycol, polyethylene glycols, propylene glycol, and polypropylene glycols. U.S. Pat. No. 3,250,813 to R. J. Stephenson, for instance, discloses a process which comprises a reaction between an allylic alcohol and itself or another alcohol in the presence of, as catalyst, a cuprous salt and, as cocatalyst, an acidic material such as a trivalent inorganic acid, a Lewis acid, a sulfonic acid, or an acid ion exchange resin. U.S. Pat. No. 3,250,814 describes a process for the preparation of allylic ethers from diallyl ethers and alcohols using the same catalyst system.

The present invention provides an improvement upon the prior art process for the preparation of higher allylic ethers from higher allylic alcohols, specifically an improvement upon the selectivity of the process for the production of allylic ethers of the alkylene and polyalkylene glycols. As expressed in the disclosures of the prior art, the allylic alcohols react only with other alcohols (and glycols) but also react with themselves. "Dimerization" reactions involving the allylic alcohol reactant (and often also the allylic ether product) are commonly the greatest factor reducing the selectivity of a process intended for the preparation of the desired allylic ethers. Both of these reactions are termed dimerization because the resulting molecule combines two of the allylic alcohol molecules. Investigations have shown that when prior art practices are applied to the reaction of the above-specified higher allylic alcohols with alkylene glycols, allylic alcohol dimer products account for as much as twenty percent of the final ether product, representing not only a loss of allylic alcohol reactant but also a source of product contamination.

Accordingly, a process improvement which increases the selectivity of the allylic alcohol reaction for the production of the alkylene glycol ethers would be highly desirable.

In one respect, the invention relates to the discovery that the presence of a certain solvent in a certain minimum quantity in the reaction mixture of the process for the preparation of allylic ethers of alkylene glycols can substantially enhance the selectivity of the desired etherification reaction. It is known in the art (for example, from the disclosure of the aforementioned U.S. Pat. No. 3,250,813) that certain of the solvents now found to be suitable for this purpose have previously been added to allylic alcohol reactions as azeotroping agents. In this respect, it has been reported that azeotroping agents may improve the process performance by removing (through evaporation) water formed in the course of etherification reactions. In the processing of higher carbon number allylic alcohols, under conditions specified for practice of this invention, however, the presence of water in the reaction mixture is not a disadvantage and there is no incentive for its azeotropic removal. Moreover, under this invention, it is necessary that the solvent remain in the reaction medium in substantial quantity throughout the course of the process. The requirement of the invention for the presence of relatively large proportions of solvent throughout the process is inconsistent with quantities of solvent reasonably employed for azeotrope formation with water and, more importantly, with the evaporation and removal of the solvent over the course of the conventional process.

SUMMARY OF THE INVENTION

It has now been found that the selectivity of the reaction of higher carbon number allylic alcohols with $C_2$ and $C_3$ alkylene glycols and their polyalkylene glycols for the production of allylic ethers is enhanced if the reaction is carried out in a two phase reaction mixture and in the presence of a solvent for the allylic alcohol reactant and the ether product. More specifically, in a process for the production of allylic ethers of the alkylene and polyalkylene glycols, which comprises a step for the reaction of one or more higher (i.e., $C_6$ to $C_{20}$) allylic alcohols with an alkylene glycol reactant comprising one or more $C_2$ or $C_3$ alkylene or polyalkylene glycols in the presence of a cuprous salt catalyst and an acidic cocatalyst, the invention is the improvement which comprises carrying out the reaction in the presence of a solvent which is substantially miscible in a nonpolar liquid phase which comprises substantially all of the allylic alcohol reactant and the allylic ether product, but which does not significantly increase the miscibility of the allylic alcohol and the allylic ether in a nonpolar liquid phase comprising substantially all of the alkylene glycol reactant.

The process improvement of this invention also requires that the reaction be carried out in the presence of a specified critical minimum quantity of the solvent.

Practice in accordance with the invention substantially reduces the formation in such a process of dimer products resulting from the reaction of the allylic alcohol reactant with itself or with the product allylic ethers.

DESCRIPTION OF THE PREFERRED EMBODIMENTS

The invention is generally applicable to any process in which allylic ethers of alkylene or polyalkylene glycols are prepared by reaction of higher (i.e., $C_6$ to $C_{20}$) allylic alcohols with $C_2$ or $C_3$ alkylene or corresponding polyalkylene glycols in a two phase reaction mixture and in the presence of a cuprous salt catalyst and an acid cocatalyst.

The allylic alcohol reactant suitably comprises one or more of the higher aliphatic allylic alcohols, having carbon numbers in the range from about 6 to 20. Suitable allylic alcohols can be represented by the formula

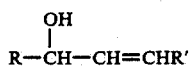

Wherein R is hydrogen, an alkyl group or an alkenyl group, R' is hydrogen, an alkyl group or an alkenyl group, and the sum of the number of carbon atoms in R and R' is from 3 to 17. Most preferably, R and R' are each independently hydrogen or alkyl. It is apparent that at most one of the R and R' groups can be hydrogen. The alkyl or alkenyl groups represented by R and R' are suitably each independently of either linear, branched or cyclic structure. Preferably, the alcohol has either a branched or linear (straight-chain) carbon structure, while a reactant with a linear carbon structure is considered most preferred.

The restriction of the invention to allylic alcohols having a carbon number of from 6 to 20, is considered a critical element of the invention. Allylic alcohol reactants having carbon numbers in the range from about 8 to 16 are preferred.

Most preferably, the invention utilizes an allylic alcohol reactant having the indicated molecular formula wherein R is hydrogen and R'0 is alkyl or alkenyl, particularly alkyl. This class of reactants include the 2-alkene-1-ol compounds, that is, compounds wherein R' is a linear alkyl group. The invention has been observed to afford a relatively high degree of process improvement when applied to such compounds.

Specific examples of allylic alcohols which are suitably employed as reactants in the process of this invention include 2-hexen-1-ol, 1-hexen-3-ol, 2-hexen-4-ol, 3-hexen-2-ol, 2-octen-1-ol, 2-nonen-1-ol, 2-decen-1-ol, 1-decen-3-ol, 2-dodecen-1-ol, 2-dodecen-4-ol, 1-dodecen-3-ol, 5-dodecen-4-ol, 2-tridecen-1-ol, 2-tetradecen-1-ol, 1-tetradecen-3-ol, and 2-hexadecen-1-ol.

The invention is very suitably applied to mixed allylic alcohol reactants, for instance mixtures of one or more 2-alkene-1-ol compounds with other allylic alcohols having different molecular structure.

The alkylene glycol reactant suitably comprises one or more compounds of the formula HO—(CH$_2$—CH(CH$_3$)—O)$_x$—H, where x is an integer, preferably an integer from 1 to about 20, more preferably from 1 to about 12, and most preferably from 1 to about 6. Specific examples include ethylene glycol, diethylene glycol, tetraethylene glycol, propylene glycol, dipropylene glycol, and the like. Polyethylene glycols are particularly preferred, for instance, ethylene glycol, diethylene glycol, triethylene glycol, and tetraethylene glycol. The use in the invention of a reactant consisting essentially of ethylene glycol is very suitable.

The alkylene glycol reactant is preferably employed in the invention in molar excess over the allylic alcohol reactant. A molar ratio of alkylene glycol reactant to allylic alcohol reactant of at least about 1.5 to 1 is particularly preferred, while a molar ratio of at least about 2 to 1 is considered more preferred.

Among the general class of alcohols which are known to undergo reaction with allylic alcohols, the alkylene and polyalkylene glycols are considered particularly susceptible to participation in dimerization reactions which reduce process selectivity to the desired allylic ethers. This susceptibility is the result of both ends of the glycol molecule having hydroxyl groups which are available for reaction with two allylic alcohol molecules. In this respect, the performance of the invention in minimizing dimerization is considered particularly significant and surprising.

For purposes of the invention, the allylic alcohol reactant and the alkylene glycol reactant are necessarily contacted in the presence of a cuprous salt catalyst. Cuprous salts known in the art as catalysts for etherification reactions of the allylic alcohols are generally suitable for use in the invention. Specific mention may be made of cuprous halides such as cuprous chloride and cuprous bromide, as well as cuprous sulfite, cuprous sulfide, cuprous acetate, cuprous p-toluenesulfonic acid, cuprous cyanide, cuprous oxide, cuprous thiocyanate, and cuprous triflate.

Likewise, the acidic cocatalyst is suitably one which is known for use in related prior art processes.

The sulfonic acids form a particularly preferred class of acidic cocatalysts. Specific examples of sulfonic acid cocatalysts include the inorganic sulfonic acids such as sulfuric acid and sulphamic acid, as well as organic sulfonic acids such as methanesulfonic acid, benzenesulphonic acid, p-toluenesulphonic acid, and trifluorotoluenesulfonic acid. Still other examples of suitable sulfonic acid cocatalysts include acid resins containing sulfonic acid groups, such as sulfonated styrene polymers or copolymers, e.g., copolymers with divinylbenzene. Sulfuric acid is considered a most preferred cocatalyst for use in the invention.

Lewis acids are also known in the art to serve as cocatalysts for the reaction. Suitable Lewis acid cocatalyst include, for example, the halides (particularly the fluorides and chlorides) and the perchlorates, of zinc, tin, boron, and aluminum.

Other suitable acidic cocatalysts include phosphoric acid, hydrochloric acid, and perchloric acid.

The cuprous salt catalyst and acidic cocatalyst are applied in catalytically effective amounts. Absolute and relative proportions of the two components are not narrowly critical. Preferably, catalyst quantities are selected which will afford acceptable reaction rate, for example, essentially complete (e.g., 90% or greater) conversion in about 12 hours or less, particularly in about 8 hours or less, at temperatures of about 100° C. or greater. Catalyst and cocatalyst quantities are known to have a significant influence upon reaction rate and a lesser influence upon reaction selectivity. Optimum amounts of the catalyst components will vary with the strength of the particular acid, and the relative quantities of reactants and solvent. However, in general, a particular preference can be expressed for a quantity of cuprous salt which is in the range from about 0.1 to 10 percent by mol, calculated on mols of allylic alcohol reactant. The acidic catalyst is preferably (but not necessarily) applied in a quantity such that the number of equivalents of acid exceeds the number of mols of cuprous salt. An acid concentration of at least about 0.05 equivalents per liter of total reaction mixture has been found to be very suitable for strong acids such as sulfuric.

For purposes of the invention, the reaction between the allylic alcohol and alkylene glycol reactants is necessarily carried out in the presence of an added solvent (i.e., a solvent other than the reactants and products.) In broad terms, the solvent is suitably one which has significant solubility for the allylic alcohol and the allylic ether product, but is essentially immiscible with the alkylene glycol reactant. In practice, the contact between the allylic alcohol reactant and the alkylene glycol reactant results in a two phase mixture, with one phase consisting essentially of the alkylene glycol reactant and water which forms in the course of the etherification reaction, and the other phase consisting essentially of the allylic alcohol reactant and the allylic ether product. The solvent which is introduced into the reaction mixture for purposes of this invention is necessarily one which will partition essentially only into the allylic alcohol/allylic ether phase of this mixture. The solvent does not change the two phase character of the reaction system. The solvent is also inert, in the sense that it does not, under the conditions of the invention, directly participate to a meaningful extent in any reaction with other components of the reaction mixture.

Preference can be expressed for use as the added solvent in the invention of hydrocarbon solvents, including both aromatic and aliphatic compounds, as well as hydrocarbyl ethers and chlorinated hydrocarbons. Specific examples of aliphatic hydrocarbon solvents include the alkanes having carbon numbers in the range from about 5 to 10, for instance, heptane and the petroleum ethers. Specific examples of preferred aromatic solvents include toluene, benzene, xylene, and mixtures thereof. Specific examples of preferred chlorinated hydrocarbon solvents include chlorobenzene, methylene chloride, carbon tetrachloride, 1,2-dichloroethane, and chloroform. Other preferred solvents for use in the invention include hydrocarbyl ethers, for instance, diethyl ether methyl acetate and ethyl acetate.

Particularly preference is given to a solvent selected from the group consisting of toluene, benzene, xylene, chlorobenzene, diethyl ether, $C_5$ to $C_{10}$ aliphatic hydrocarbons, dichloromethane chloroform, and carbon tetrachloride. The use of toluene and benzene solvents is considered most preferred.

Mixtures of solvents are also suitable.

It has been found to be critical to the process of the invention that a substantial excess of the added solvent be present in the reaction mixture. In this regard, it is necessary that the solvent be present in a quantity which is at least about three times by weight that of the allylic alcohol reactant (and, as the reaction proceeds, the allylic ether product). The use of lesser amounts of solvent does not result in the desired improvement in process selectivity. A quantity of solvent which is at least about five times that of the allylic alcohol reactant/allylic ether is particularly preferred, and a quantity of solvent which is at least about eight times by weight that of the allylic alcohol reactant/allylic ether is considered most preferred. Substantially greater quantities of solvent, for instance up to about twenty times by weight that of the allylic alcohol and allylic ether, can be used if desired.

In practice, a mixture is made of the allylic alcohol reactant, the alkylene glycol reactant, the cuprous salt catalyst, and the acidic cocatalyst with the solvent. The mixture is then heated to commence the etherification reaction.

Apart from the presence of the particular solvent in the quantity specified, the process is suitably carried out using procedures, equipment, and conditions of the prior art.

The process is necessarily conducted at elevated temperature. Temperatures in the range from about 50° to 180° C. are preferred, while those in the range from about 80° to 120° C. have generally been found to be most preferred. Process pressure suitably varies over a wide range, with atmospheric or greater pressures generally preferred. The pressure is necessarily at least that which is sufficient to maintain the glycol and allylic alcohol reactants, the allylic ether product, the catalyst components, and the solvent substantially in the liquid phases. Process pressures in the range from about 0 to 100 psig are considered most preferred.

The two-phase reaction mixture of the process is preferably well agitated during the course of the reaction. Agitation of the mixture has been observed to be an important factor in maintaining a desired reaction rate.

In operation under preferred conditions, the invention yields the desired allylic ethers of the alkylene glycols in high conversion and high yield. The product generally contains a mixture of different allylic ethers, having different double bond and ether oxygen bond positions. Recovery of the ethers from the product mixture is suitably accomplished by conventional means, for example, by filtration to separate solid components, followed by multiple distillations to separate and recover product, solvent, and unreacted allylic alcohols and alkylene glycols.

The invention is further described in the following examples and which are intended to illustrate certain preferred aspects of the invention and not to limit its broader scope. Comparative experiments are also described which illustrate the critical limitations of the invention.

For each of the examples and comparative experiments, the allylic alcohol and alkylene glycol reactants and the solvent were mixed in a glass reactor. Cuprous chloride catalyst and acidic cocatalyst were added and the reaction mixture was quickly brought to the desired temperature. The reactor was stirred and its temperature maintained essentially constant over the course of the reaction. At the end of the specified reaction time, the reactor contents were cooled and the product analyzed (by GC and/or GC/mass spectroscopy methods) to determine conversion of allylic alcohol, and selectivities to the desired ethers and to the dimer byproducts.

EXAMPLES 1-11

In each of examples 1-11, a 2-decen-1-ol reactant was reacted with ethylene glycol in a toluene solvent. Procedures followed in these examples are described in Table 1a and results are given in Table 1b.

The Amberlite acid cocatalyst used in examples 1 and 2 was an Amberlite IR 120H resin. A phase transfer catalyst—tetrabutylammonium hydrogen sulfate (0.1 grams in examples 2 and 3 and 0.5 grams in examples 4, 8, and 9) or cetyl tetramethylammonium sulfate—was added without significant influence upon process performance.

TABLE 1a

| no. | grams allylic alcohol | grams ethylene glycol | acidic cocatalyst (grams) | grams CuCl | ml toluene |
|---|---|---|---|---|---|
| 1 | 5 | 20 | Amberlite (1.5) | 0.1 | 60 |
| 2 | 5 | 20 | Amberlite (1.5) | 0.1 | 60 |
| 3 | 5 | 20 | sulfuric (0.4) | 0.1 | 60 |
| 4 | 20 | 80 | sulfuric (2.0) | 0.5 | 200 |
| 5 | 20 | 80 | sulfuric (2.0) | 0.5 | 200 |
| 6 | 20 | 80 | sulfuric (2.0) | 0.5 | 200 |
| 7 | 20 | 80 | sulfuric (2.0) | 0.5 | 200 |
| 8 | 20 | 80 | sulfuric (2.0) | 0.5 | 200 |
| 9 | 20 | 80 | sulfuric (2.0) | 0.5 | 200 |
| 10 | 20 | 80 | sulfuric (2.0) | 0.5 | 200 |
| 11 | 20 | 80 | sulfuric (2.0) | 0.5 | 200 |

TABLE 1b

| no. | reaction time (hr.) | reaction temp. (°C.) | alcohol conversion (%) | allylic ether (%) | dimer (%) | diene (%) |
|---|---|---|---|---|---|---|
| 1 | 48 | 110 | 81 | 98 | 0 | <2 |
| 2 | 48 | 105 | 48 | 99+ | 0 | <1 |
| 3 | 7 | 95 | 43 | 99+ | 0 | <1 |
| 4 | 3.5 | 108 | 93 | 97+ | 0 | <3 |
|   | 10 | 108 | 95 | 97 | 0 | <3 |
| 5 | 3.5 | 109 | 77 | 95+ | 0 | <5 |
|   | 6.5 | 109 | 95+ | 97+ | 0 | <3 |
| 6 | 3.5 | 110 | 82 | 95+ | 0 | <5 |
|   | 6.5 | 110 | 94+ | 96+ | 0 | <4 |
| 7 | 3 | 110 | 95+ | 95+ | 0 | <5 |
|   | 6 | 110 | 95+ | 96+ | 0 | <4 |
| 8 | 2 | 110 | 81 | 95+ | 0 | <5 |
|   | 4 | 100 | 95+ | 95+ | 0 | <5 |
|   | 6 | 110 | 99 | 92 | 5 | 3 |
| 9 | 2 | 110 | 82 | 95+ | 0 | — |
|   | 5 | 110 | 99.9 | 99.8 | 0 | 0.2 |
| 10 | 2 | 105 | 59 | 95+ | 0 | <5 |
|   | 2 | 105 | 99 | 98.3 | 0 | 1.7 |
| 11 | 2 | 98 | 80 | 99+ | 0 | 0 |
|   | 4 | 110 | 95+ | 99+ | 0 | 0 |
|   | 5 | 110 | 95+ | 99+ | 0 | 0 |
|   | 6 | 110 | 95+ | 98 | 0 | 2 |

Comparative Experiments A-F

A series of comparative experiments, not in accordance with the invention, were carried out with a sulfolane reaction solvent. The presence of the sulfolane solvent resulted in a homogeneous, single liquid phase reaction mixture and in the formation of large amounts of dimer and diene byproducts. In other respect, the same procedures were followed in these experiments as in examples 1–11. Process conditions are described in Table 2a and results are given in Table 2b.

TABLE 2a

| no. | grams allylic alcohol | grams ethylene glycol | acidic cocatalyst (grams) | grams CuCl | ml sulfolane | temp. (°C.) |
|---|---|---|---|---|---|---|
| A | 5 | 20 | Amberlite (1.5) | 0.1 | 120 |   |
| B | 5 | 20 | Amberlite (1.5) | 0.1 | 60 |   |
| C | 5 | 20 | sulfuric (0.4) | 0.1 | 120 |   |
| D | 5 | 20 | sulfuric (0.4) | 0.1 | 60 |   |
| E | 5 | 20 | sulfuric (0.8) | 0.1 | 120 |   |
| F | 5 | 20 | sulfuric (0.4) | 0.1 | 60 |   |

TABLE 2b

| no. | reaction time (hr.) | reaction temp. (°C.) | alcohol conversion (%) | allylic ether (%) | dimer (%) | diene (%) |
|---|---|---|---|---|---|---|
| A | 5 | 99 | 94 | 87 | 4 | 9 |
| B | 7 | 110 | 95+ | 20 | 21 | 69 |
| C | 2 | 99 | 93 | 68 | — | 32 |
| D | 2 | 130 | 95+ | <10 | ca. 15 | >70 |
| E | 5 | 100 | 95+ | ca. 40 | ca. 10 | ca. 48 |
| F | 1 | 98 | 98+ | 88 | <3 | 12 |
|   | 2 | 98 | 98+ | 41 | 4 | 55 |

EXAMPLES 12–29

In each of examples 12–29, a 2-hexen-1-ol reactant was reacted with ethylene glycol in a benzene solvent. Procedures followed in these examples are described in Table 3a and results are given in Table 3b. All reactions were run under reflux conditions at one atmosphere and a temperature in the range from 80° to 90° C.

TABLE 3a

| no. | grams allylic alcohol | grams ethylene glycol | acidic cocatalyst (grams) | grams CuCl | ml benzene |
|---|---|---|---|---|---|
| 12 | 5 | 20 | Amberlite (1.5) | 0.05 | 45 |
| 13 | 5 | 20 | Amberlite (1.5) | 0.05 | 45 |
| 14 | 5 | 10 | sulfuric (0.4) | 0.05 | 30 |
| 15 | 5 | 10 | sulfuric (0.4) | 0.05 | 30 |
| 16 | 5 | 10 | sulfuric (0.8) | 0.05 | 60 |
| 17 | 5 | 10 | sulfuric (0.4) | 0.05 | 60 |
| 18 | 5 | 10 | sulfuric (0.4) | 0.1 | 60 |
| 19 | 5 | 10 | sulfuric (0.4) | 0.1 | 60 |
| 20 | 5 | 20 | sulfuric (0.4) | 0.1 | 60 |
| 21 | 5 | 20 | sulfuric (0.4) | 0.1 | 60 |
| 22 | 5 | 20 | Amberlite (1.5) | 0.1 | 60 |
| 23 | 5 | 20 | sulfuric (0.4) | 0.1 | 60 |
| 24 | 5 | 20 | sulfuric (0.4) | 0.1 | 60 |
| 25 | 5 | 20 | Amberlite (1.5) | 0.1 | 60 |
| 26 | 5 | 20 | Amberlite (1.5) | 0.1 | 60 |
| 27 | 5 | 20 | Amberlite (1.5) | 0.6 | 60 |
| 28 | 5 | 20 | Amberlite (1.5) | 0.6 | 60 |
| 29 | 5 | 20 | Amberlite (1.5) | 0.1 | 60 |

TABLE 3b

| no. | reaction time (hr.) | alcohol conversion (%) | selectivity allylic ether (%) | dimer (%) |
|---|---|---|---|---|
| 12 | 2 | 66 | 97.4 | 2.6 |
| 13 | 26 | 92 | 96.2 | 3.8 |
| 14 | 2 | 97 | 94 | 6 |
| 15 | 5 | 98 | 91.4 | 8.6 |
| 16 | 2 | 89 | 97.4 | 2.6 |
| 17 | 5 | 97 | 98 | 2 |
| 18 | 3 | 97 | 98.5 | 1.5 |
| 19 | 3 | 96 | 98.5 | 1.5 |
| 20 | 1 | 90 | 99 | 1 |
| 21 | 3 | >98 | 98.3 | 1.7 |
| 22 | 16 | >98 | 98.5 | 1.5 |
| 23 | 1 | 70 | 93 | 7 |
| 24 | 6 | >98 | 98.5 | 1.5 |
| 25 | 2 | 87 | >99 | trace |
| 26 | 6 | >99 | 99 | 1 |
| 27 | 2 | 79 | 99 | trace |
| 28 | 6 | >99 | 95 | 5 |
| 29 | 14 | >99.9 | 97.3 | 2.7 |

A comparison of the results of examples 14 with those for example 15 and of the results of example 27 with those of example 28 are believed to illustrate the importance of maintaining in the reaction medium the specified quantity of the solvent. Solvent vapors were lost as the reaction proceeded in the experimental equipment under solvent vapor reflux and the quantity of solvent in the reactor noticeably decreased. At the end of the longer reactions (5 hours in the case of example 15 and 6 hours in the case of example 28) the extent of solvent boil-off is believed to have been such that the process did not at that time satisfy the requirements of the invention in terms of the quantity of solvent present.

Comparative Experiments G–M

Comparative experiments G–M further illustrate the importance of maintaining the specified quantity of solvent in the reaction mixture. In these experiments, 2-hexen-1-ol was reacted with ethylene glycol in the presence of quantities of solvent (benzene) lower than those specified for use in this invention. Procedures followed in these examples are described in Table 4a and results are given in Table 4b. All reactions were run under reflux conditions at one atmosphere and a temperature in the range from 80° to 90° C.

TABLE 4a

| no. | grams allylic alcohol | grams ethylene glycol | acidic cocatalyst (grams) | grams CuCl | ml benzene |
|---|---|---|---|---|---|
| G | 5 | 20 | sulfuric (0.2) | 0.05 | 16 |
| H | 5 | 9.3 | sulfuric (0.4) | 0.1 | 16 |
| I | 5 | 9.3 | sulfuric (0.4) | 0.1 | 16 |
| J | 5 | 20 | sulfuric (0.8) | 0.1 | 16 |
| K | 5 | 9.3 | sulfuric (0.4) | 0.1 | 16 |
| L | 5 | 9.3 | sulfuric (0.4) | 0.1 | 16 |
| M | 5 | 9.3 | Amberlite (0.8) | 0.1 | 16 |

TABLE 4b

| no. | reaction time (hr.) | alcohol conversion (%) | selectivity allylic ether (%) | dimer (%) |
|---|---|---|---|---|
| G | 3 | 57 | 90.4 | 9.6 |
| H | 1 | 96 | 94 | 6 |
| I | 3 | 99 | 80 | 20 |
| J | 2 | 98 | 95 | 5 |
| K | 1 | 66 | 96.3 | 3.7 |
| L | 2 | 93 | 89 | 11 |
| M | 3 | 96 | 94 | 6 |

At comparable conversion levels, the process selectivities for the desired allylic ethers in experiments G–H are substantially less than the ether selectivities in examples 12–29. For instance, with the exception of the solvent quantity present, example 19 was run under essentially the same conditions and to the same conversion (96%) as experiment H. Yet, example 19 resulted in the production dimer with a selectivity of only 1.5%, whereas the dimer selectivity in experiment H was 6%.

EXAMPLES 30–32 AND COMPARATIVE EXPERIMENT N

For each of examples 30–32 and comparative experiment N, a 1-hexen-3-ol reactant (rather than 2-hexen-1-ol) was reacted with ethylene glycol in a benzene solvent. Procedures followed in these examples are described in Table 5a and results are given in Table 5b. All reactions were run under reflux conditions at one atmosphere and a temperature in the range from 80° to 90° C.

Comparative experiment N again illustrates the importance of maintaining a high solvent level in the process. At about the same conversion level, the dimer formation in the comparative experiment was substantially greater (3.2%) than in examples 31 and 32 (1.7% and <1%, respectively).

TABLE 5a

| no. | grams allylic alcohol | grams ethylene glycol | acidic cocatalyst (grams) | grams CuCl | ml benzene |
|---|---|---|---|---|---|
| 30 | 5 | 20 | sulfuric (0.4) | 0.1 | 60 |
| 31 | 5 | 20 | sulfuric (0.4) | 0.1 | 60 |
| 32 | 5 | 20 | Amberlite (1.5) | 0.1 | 60 |
| N | 5 | 9.3 | sulfuric (0.4) | 0.1 | 16 |

TABLE 5b

| no. | reaction time (hr.) | alcohol conversion (%) | selectivity allylic ether (%) | dimer (%) |
|---|---|---|---|---|
| 30 | 1 | 81 | >99.9 | trace |
| 31 | 3 | >99.5 | >98 | 1.7 |
| 32 | 16 | >99 | >99 | <1 |
| N | 2 | 99 | 96.8 | 3.2 |

EXAMPLES 33 AND 34

Examples 33 and 34 illustrate that the performance of the the added solvent in this invention is not the result of its ability to form an azeotrope with water formed in the process. To illustrate that water removal does not enhance the reaction selectivity for processing of higher ($C_6+$) allylic alcohol reactants, two examples were carried out utilizing 2-hexen-ol reactant and a toluene solvent. The two examples were run under the same process conditions, except that in Example 33 the reaction mixture was continuously sparged with nitrogen to evaporate a solvent/water azeotrope, while the reaction mixture in Example 34 was not sparged. Both examples were run at 80°-90° C. Process conditions are shown in Table 6a and results in Table 6b.

TABLE 6a

| no. | grams allylic alcohol | grams ethylene glycol | acidic cocatalyst (grams) | grams CuCl | ml toluene | $N_2$ sparge |
|---|---|---|---|---|---|---|
| 33 | 5 | 10 | sulfuric (0.4) | 0.1 | 60 | YES |
| 34 | 5 | 10 | sulfuric (0.4) | 0.1 | 60 | NO |

TABLE 6b

| no. | reaction time (hr.) | alcohol conversion (%) | selectivity allylic ether (%) | selectivity dimer (%) |
|---|---|---|---|---|
| 33 | 3 | 98 | 98.4 | 1.6 |
| 34 | 3 | 98 | 98.6 | 1.4 |

EXAMPLE 35

Following the general procedure, 100 grams of trans-2-decene-1-ol were contactyed with 400 grams of triethylene glycol in the presence of 10 ml of sulfuric acid, 2.5 grams of cuprous chloride, and one liter of toluene. After six hours reaction at 100° C., conversion of the allylic alcohol reached about 99%. Process selectivity to allylic ethers was about 98% with the remaining 2% representing dimers and a trace of dienes.

I claim as my invention:

1. In a process for the preparation of allylic ethers which comprises contacting and reacting an allylic alcohol alcohol reactant comprising one or more $C_6$ to $C_{20}$ allylic alcohols with a glycol reactant which comprises one or more $C_2$ or $C_3$ alkylene glycols and their polyalkylene glycols in the presence of a cuprous salt catalyst and an acidic cocatalyst, the improvement which comprises contacting the allylic alcohol and alkylene glycol reactants in an agitated reaction mixture containing a solvent for the allylic alcohol reactant and the ether product which is substantially immiscible with the alkylene glycol reactant, said solvent being present and maintained in the reaction mixture in a quantity by weight which is at least about three times the weight of the allylic alcohol reactant and as the reaction proceeds, of the allylic ether product.

2. The process of claim 1, wherein the solvent is present in a quantity by weight which is at least about five times the weight of the allylic alcohol reactant and as the reaction proceeds, of said ether products.

3. The process of claim 1, wherein the solvent is selected from the group consisting of toluene, benzene and xylene.

4. The process of claim 3, wherein the solvent is present in a quantity by weight which is at least about five times the weight of the allylic alcohol reactant and as the reaction proceeds, of said ether products.

5. The process of claim 1, wherein the solvent is selected from the group consisting of $C_5$ to $C_{10}$ alkanes.

6. The process of claim 5, wherein the solvent is present in a quantity by weight which is at least about five times the weight of the allylic alcohol reactant and as the reaction proceeds, of said ether products.

7. The process of claim 1, wherein the solvent is selected from the group consisting of chloroform, 1,2-dichloroethane, methylene chloride, chlorobenzene, and carbon tetrachloride.

8. The process of claim 7, wherein the solvent is present in a quantity by weight which is at least about five times the weight of the allylic alcohol reactant and as the reaction proceeds, of said ether products.

9. The process of claim 1, wherein the solvent is diethyl ether.

10. The process of claim 9, wherein the solvent is present in a quantity by weight which is at least about five times the weight of the allylic alcohol reactant and as the reaction proceeds, of said ether products.

11. In a process for the preparation of allylic ethers which comprises contacting and reacting an allylic alcohol alcohol reactant comprising one or more $C_6$ to $C_{20}$ allylic alcohols with a glycol reactant consisting essentially of ethylene glycol in the presence of a cuprous salt catalyst and an acidic cocatalyst, the improvement which comprises contacting the allylic alcohol and glycol reactants in an agitated reaction mixture containing a solvent for the allylic alcohol reactant and the ether product which is selected from the group consisting of toluene, benzene, xylene, and mixtures thereof, said solvent being present and maintained in the reaction mixture in a quantity by weight which is at least about five times the weight of the allylic alcohol reactant and as the reaction proceeds, of the allylic ether product.

* * * * *